(12) United States Patent
Chen et al.

(10) Patent No.: US 7,008,547 B2
(45) Date of Patent: Mar. 7, 2006

(54) SOLID PHASE SENSORS

(75) Inventors: Jia Ming Chen, Plainsboro, NJ (US); Yongchi Tian, Princeton, NJ (US); Zilan Shen, West Windsor, NJ (US); Pradyumna Swain, Franklin Park, NJ (US)

(73) Assignee: Sarnoff Corporation, Princeton, NJ (US)

( * ) Notice: Subject to any disclaimer, the term of this patent is extended or adjusted under 35 U.S.C. 154(b) by 228 days.

(21) Appl. No.: 10/383,380

(22) Filed: Mar. 7, 2003

(65) Prior Publication Data

US 2003/0174563 A1  Sep. 18, 2003

Related U.S. Application Data

(60) Provisional application No. 60/364,779, filed on Mar. 14, 2002.

(51) Int. Cl.
*B44C 1/22* (2006.01)
*H01B 13/00* (2006.01)
*H01L 21/461* (2006.01)
*G01N 15/06* (2006.01)
*G01N 27/00* (2006.01)

(52) U.S. Cl. ............................ 216/11; 216/13; 216/16; 216/41; 216/56; 216/58; 216/72; 216/74; 422/50; 422/68.1; 422/82.01; 422/83; 422/98; 436/43; 436/149; 436/151; 73/1.01; 73/1.02; 438/21; 438/400; 438/689; 438/735; 29/592; 29/592.1

(58) Field of Classification Search ............... 216/11, 216/16, 13, 41, 56, 58, 72, 74; 422/50, 68.1, 422/82.01, 83, 98; 436/43, 149, 151; 73/1.01, 73/1.02; 438/21, 400, 689, 735; 29/592, 29/592.1
See application file for complete search history.

(56) References Cited

U.S. PATENT DOCUMENTS

| | | | | |
|---|---|---|---|---|
| 4,857,479 | A * | 8/1989 | McLaughlin et al. | 438/348 |
| 4,974,060 | A * | 11/1990 | Ogasawara | 257/296 |
| 4,984,038 | A * | 1/1991 | Sunami et al. | 257/301 |
| 5,795,782 | A * | 8/1998 | Church et al. | 436/2 |
| 6,363,002 | B1 * | 3/2002 | Nishimura et al. | 365/145 |
| 6,426,231 | B1 * | 7/2002 | Bayley et al. | 436/518 |
| 6,455,303 | B1 * | 9/2002 | Orwar et al. | 435/287.1 |
| 6,503,409 | B1 * | 1/2003 | Fleming | 216/56 |
| 6,861,694 | B1 * | 3/2005 | Nakamura | 257/306 |
| 6,878,989 | B1 * | 4/2005 | Izumisawa et al. | 257/328 |
| 6,921,693 | B1 * | 7/2005 | Tsuboi et al. | 438/254 |

* cited by examiner

*Primary Examiner*—Brian J. Sines
(74) *Attorney, Agent, or Firm*—William J. Burke (57) ABSTRACT

Provided is a solid phase array of electrical sensors, each comprising a channel and electrical leads for attaching to a voltage, current or resistivity meter for measuring the voltage, current or resistivity through the pore, wherein the channels are formed of a single substrate.

10 Claims, 12 Drawing Sheets

SOLID PHASE SENSORS

This application claims the priority of U.S. application Ser. No. 60/364,779, filed Mar. 14, 2002.

The present invention relates to solid phase arrays of electrical sensors, which can be used as patch clamps.

Patch clamps, which are well known and extensively utilized in the art, typically involve forming an artificial or native biological membrane segment across a tip formed from a drawn glass micropipet. Ideally, a single current-inducing membrane component is incorporated into the biological membrane, and currents from this component are measured. Such devices are described, for example, in U.S. Pat. Nos. 6,363,002, 6,426,231 and 6,455,303. These devices are typically fragile, and not susceptible to forming diverse arrays of reporter components associated with the pores of the patch clamps.

Conventional biosensors apply highly specific receptors or physiochemical reactions to determine and identify known analytes in the presence of controlled backgrounds and interference. These approaches are highly accurate and highly selective when the target analyte is specified, but are more difficult to apply when analytes are outside the list of those originally designed to be detected. The highly selective approach also places high constraints on receptor/enzyme engineering to obtain specificity to a target analyte. A new class of sensors, commonly known as artificial nose sensors, uses a complementary approach based on cross-reactive sensor arrays of less selective molecular recognizers. This approach is inspired by the superb performance of biological olfactory systems in odor detection using relatively few (approximately one thousand) olfactory receptor genes. Another technique capable of determining unspecified analytes, also inspired by biology, is stochastic sensing, the uses of a single molecule of membrane pore for detection. Arrays of stochastic sensors for cross-reactive sensing have been suggested, but implementation has been difficult due to the fragile nature of lipid membranes.

Small-scaled pores, or "nanopores," such as are fabricated according to the present invention can also be used to sequence nucleic acid. As discussed in U.S. Pat. Nos. 6,503,409 and 5,795,782, the individual shape and chemical properties of the nucleic acid bases create characteristic ion currents as these bases are pulled by an electric field through the nanopores.

The present invention provides for mass producing arrays of pores that can, for example, be used to make patch clamps, or cross-reactive arrays. Voltage differences or currents measured from the exterior of the pores to the interiors can also be used in other sensor contexts. With the solid-state character of these arrays, robust, real-time sensing is provided. The invention further provides methods of fabricating nanopores using photolithography, thereby providing Nano-Electro-Mechanical Systems (NEMS) stochastic-based, cross-reactive sensor arrays for high throughput detection and the testing of binding properties of unspecified analytes.

SUMMARY OF THE INVENTION

In one embodiment, the invention relates to a solid phase array of electrical sensors, each comprising a channel and electrical leads for attaching to a voltage, current or resistivity meter for measuring the voltage, current or resistivity through the pore, wherein the channels are formed of a single substrate or with a single surface-initiated oxidative conversion reaction. The invention further relates to bio-molecules detectors formed from such arrays.

The invention also relates to a method of forming a solid phase array of electrical sensors comprising: forming pillars on a surface of a substrate; conducting a surface-initiated oxidative conversion reaction to convert the lateral exterior of the pillars to a form more resistive to an isotropic etching process, while not converting cores of the pillars; conducting an etching process to form the channels from the cores; and forming larger cavities in the substrate beneath and connected to the channels. The method can further comprise: filling the space between the pillars with a material; and forming a smooth surface of the substrate adjacent to where the channels exit the substrate.

BRIEF DESCRIPTION OF THE DRAWINGS

FIGS. 1A–1-I illustrate an embodiment of the electrical sensor, and a process for preparing that embodiment.

DETAILED DESCRIPTION OF THE INVENTION

Figure 1:
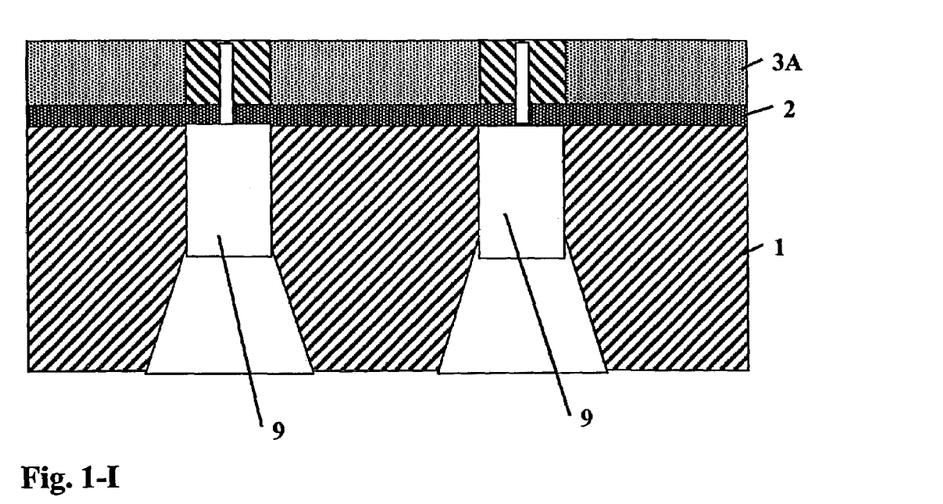
Figure 1A:
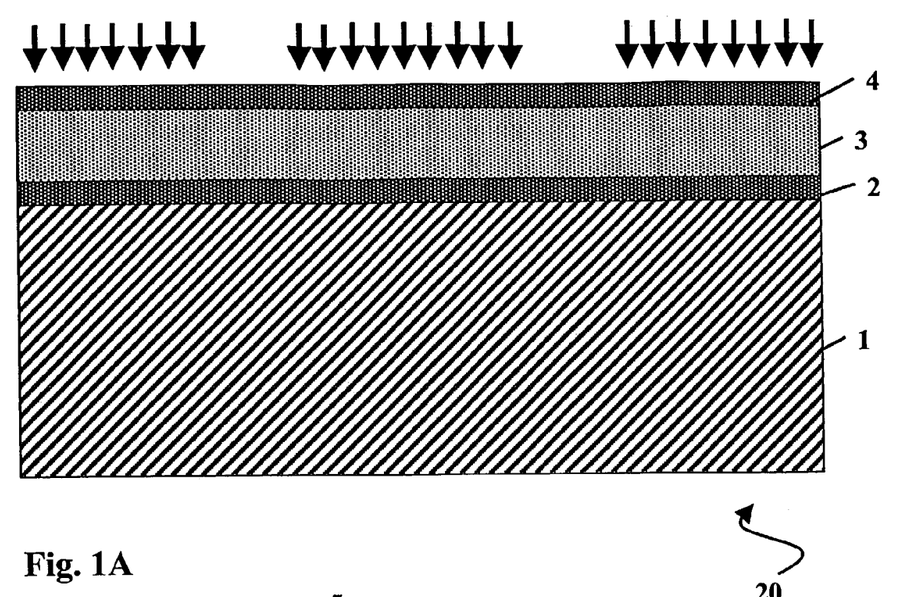

One embodiment of the construction of the devices of the invention is illustrated in FIG. 1. A sandwiched structure 20 is formed of first layer 1, second layer 2, third layer 3 and fourth layer 4. The third layer 3 material is selected to be susceptible to a surface-initiated oxidative conversion reaction, which reaction converts the material to a form more resistive to reactive ion etching processes or another isotropic etching process (a "resistive form"). A surface-initiated oxidative conversion reaction is one that initiates at the surface and serially continues inwards, allowing reaction conditions to be selected to allow for an unreacted core to remain. The material of the fourth layer 4 is selected to resist being converted by the surface-initiated oxidative conversion reaction effective to convert portions of third layer 3 to a resistive form. The second layer 2 is optional to this process, but can be selected to be resistant to a relevant anisotropic etching process, and/or to resist being converted by the surface-initiated oxidative conversion reaction that converts portions of third layer 3 to a resistive form.

Figure 1B:
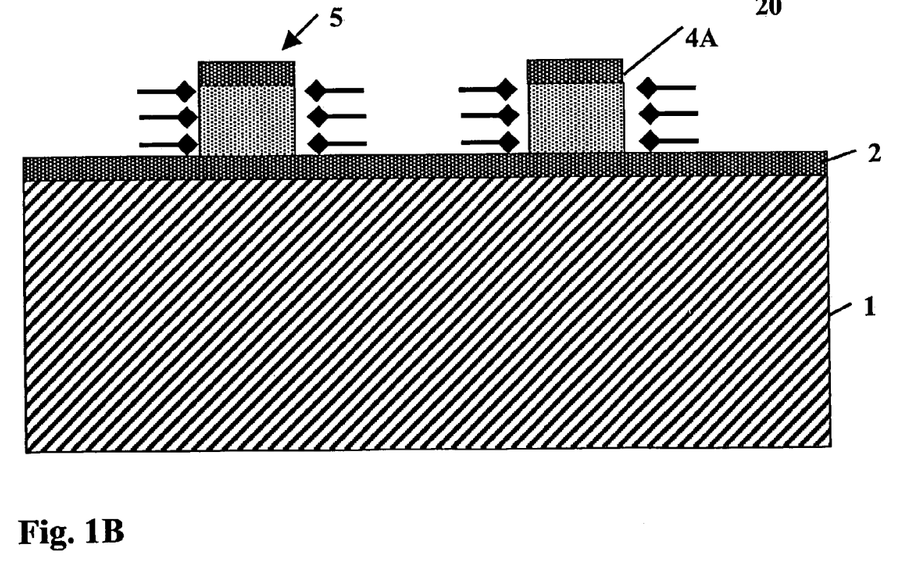
Figure 1C:
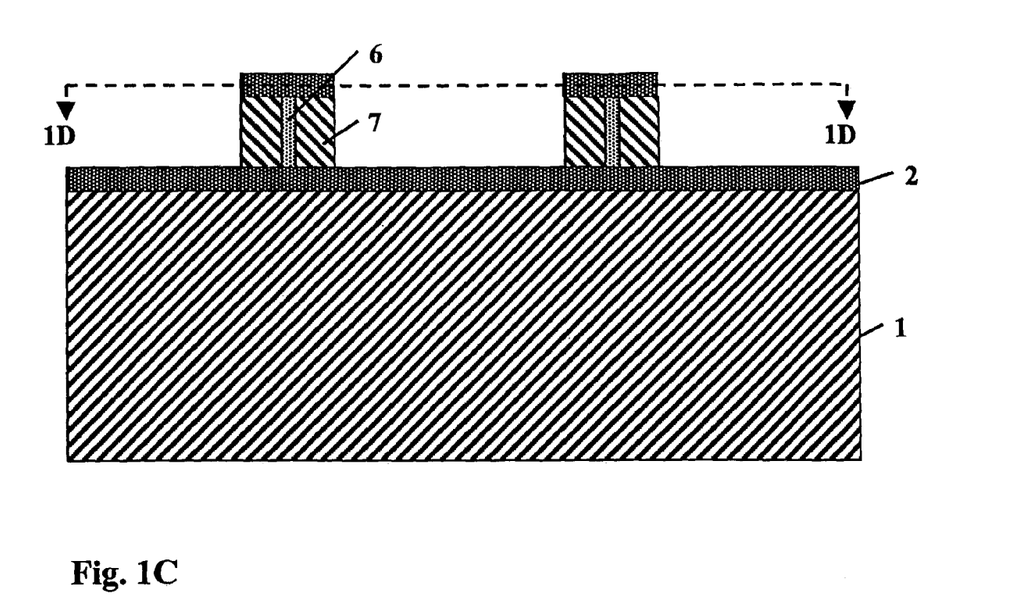
Figure 1D:
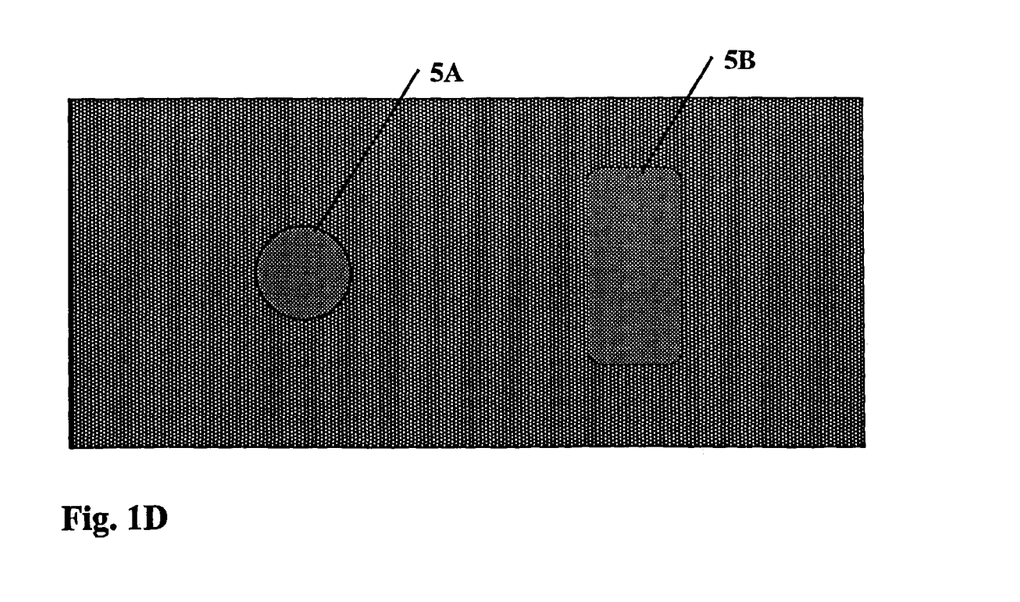

Anisotropic etching, indicated by the arrows in FIG. 1A, is conducted to form pillars 5 (shown in FIG. 1B), of a small width in a minor axis, such as about 1 to 2 microns. Where the pillars are round in cross-section, the minor axis width becomes the diameter. Circular pillar 5A and rectangular pillar 5B (having a minor axis and major axis) are illustrated in FIG. 1D. Segments 4A are left of fourth layer 4.

The surface-initiated oxidative conversion reaction is conducted to convert most of the material in the third layer to a cladding 7 of the resistive form, leaving a core 6 in the original form. The diamond-headed arrows in FIG. 1B indicate the direction in which this surface-initiated oxidative conversion reaction proceeds. The surface-initiated oxidative conversion reaction is preferably one that slows as conversion begins to occur deeper in the material, such that with appropriate control of reaction conditions the width of the unreacted core 6 can be reproducibly established.

Figure 1E:
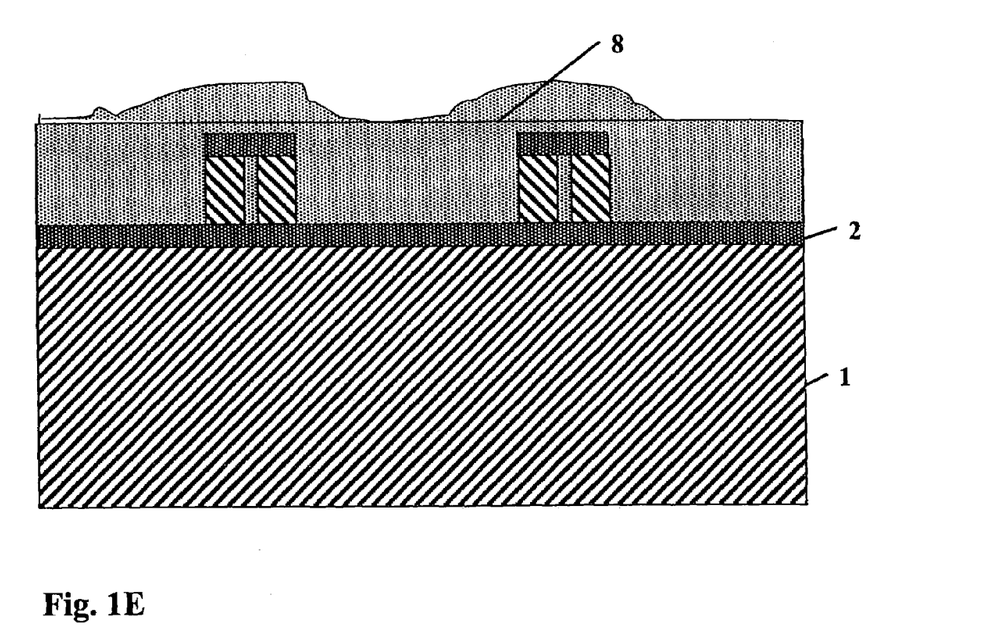
Figure 1F:
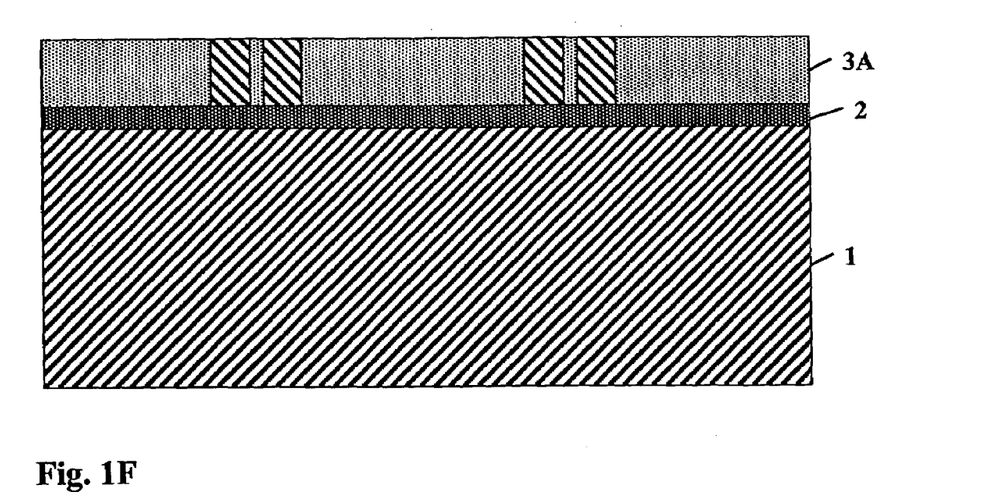

Material 8 is deposited to fill in the space between the pillars 5, to obtain the structure of FIG. 1E. The deposition process can be, for example, conformal deposition, liquid spin, electrode plating, and the like. Portions of this material 8, and optionally portions of the pillars 5, such as the segments 4A, are removed to make a planar modified third layer 3A (FIG. 1F). This deposition process is optional, as the channels formed by the processes of the invention can be used without the filling process, but such filling can add physical stability to the array.

Figure 1G:
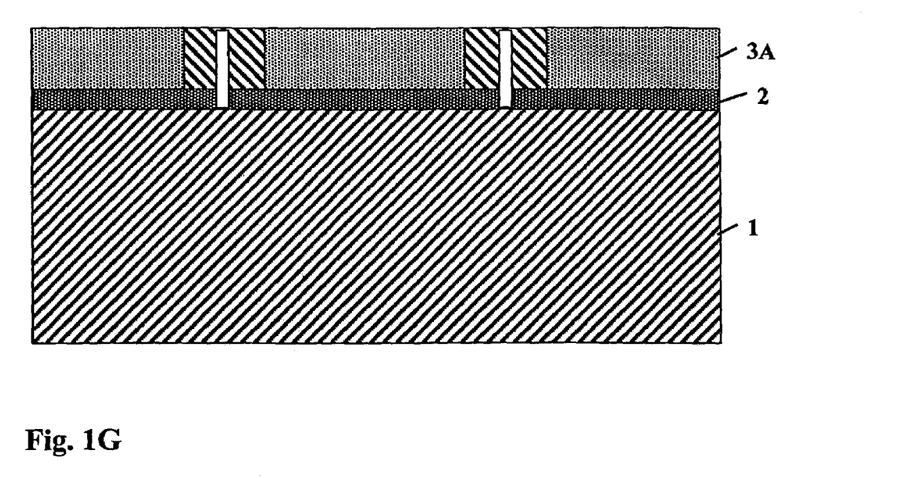
Figure 1H:
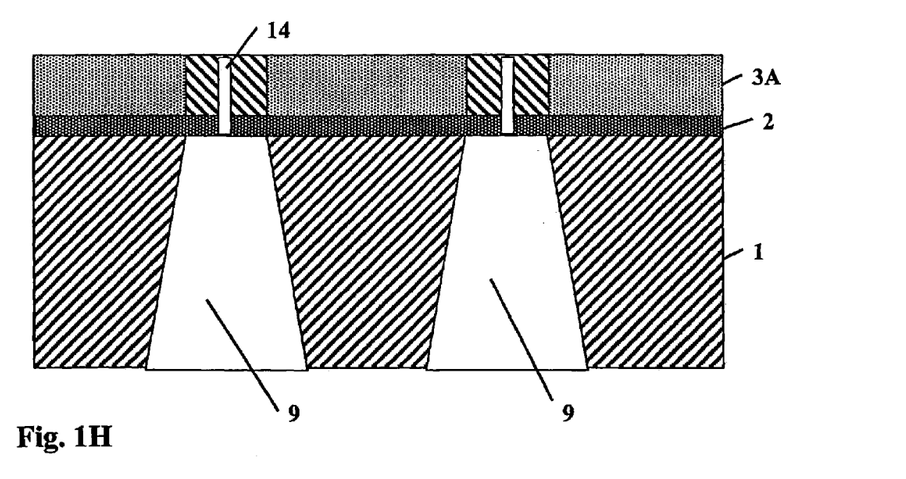

An isotropic etching technique is used to convert the cores 6 to channels (or "pores") 14, which preferably have width of from about 1 nm to about 100 nm, preferably about 5 nm to about 25 nm (FIG. 1G). Thus, in one embodiment the channels have width of 25 nm or less. Thereafter, the first layer 1 can be etched to make interior cavities 9 linked to the channels 14. As illustrated in FIG. 1H, this etching can be done by an anisotropic technique, by an isotropic technique, by combination of isotropic techniques (as illustrated in FIG. 1-I), by combinations of isotropic and anisotropic techniques.

Another embodiment of the construction of the devices of the invention is illustrated in FIG. 3. A sandwiched structure 70 is formed of first layer 51, second layer 52, third layer 53 and fourth layer 54. A surface-initiated oxidative conversion reaction is one that initiates at the surface and serially continues inwards, allowing reaction conditions to be selected to allow for an unreacted core to remain. The material of the fourth layer 54 is selected to resist being converted by the surface-initiated oxidative conversion reaction effective to convert portions of third layer 53 to a resistive form. The second layer 52 is optional to this process, but can be selected to be resistant to a relevant anisotropic etching process, and/or to resist being converted by the surface-initiated oxidative conversion reaction that converts portions of third layer 53 to a resistive form.

Figure 3A:
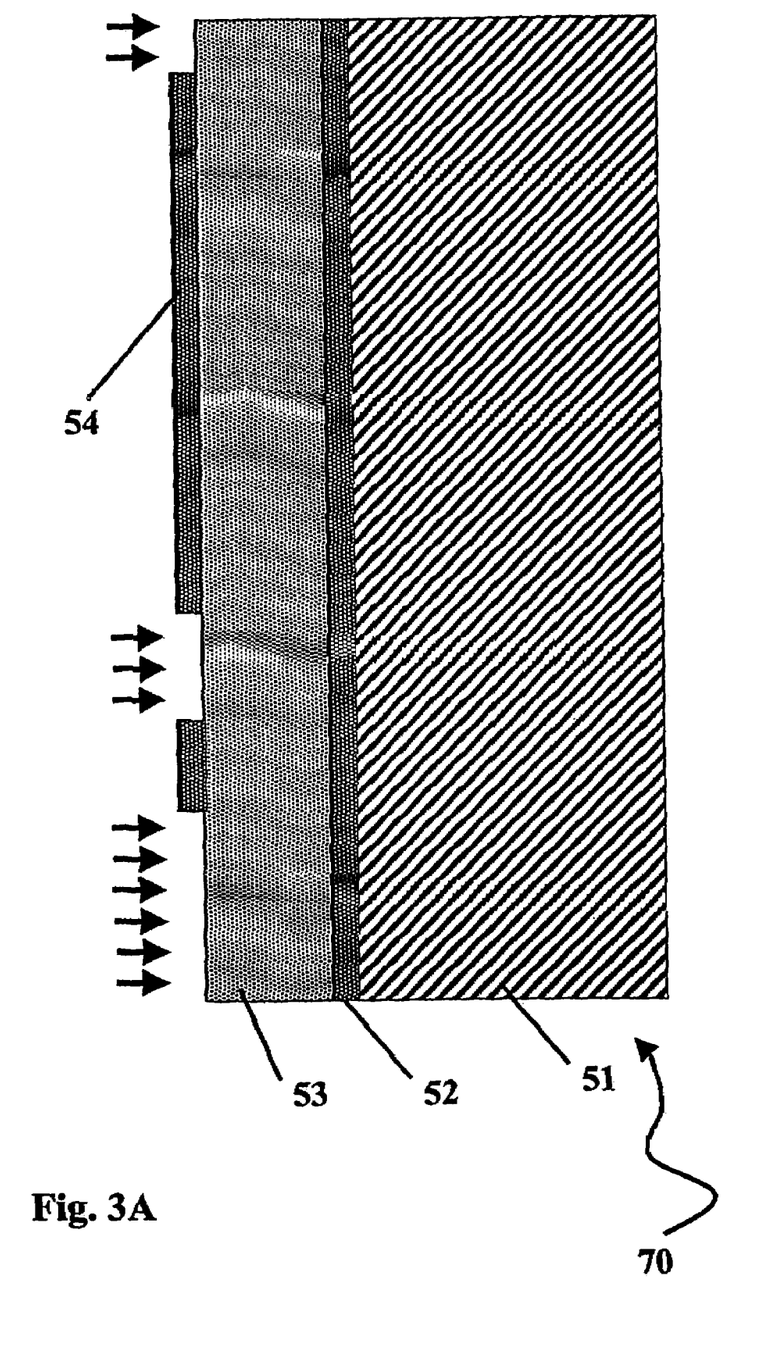
FIGS. 3A–3G illustrate another embodiment of the electrical sensor, and a process for preparing that embodiment.
Figure 3B:
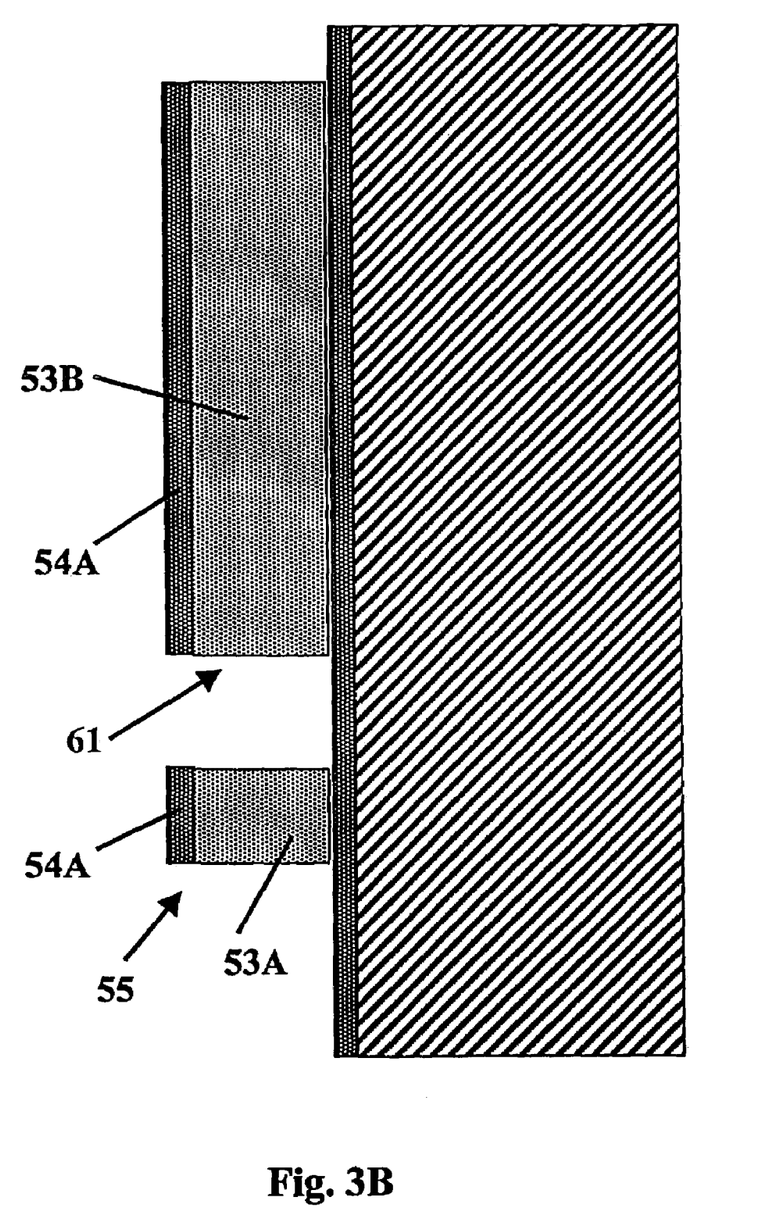

Anisotropic etching, indicated by the arrows in FIG. 3A, is conducted to form pillars 55 (shown in FIG. 3B), of illustrative width in a minor axis of from about 1 microns to about 2 microns. In this embodiment, structural segments 61 are also formed. Segments 54A are left of fourth layer 54. Segments 53A and 53B remain from original third layer 53.

Figure 3C:
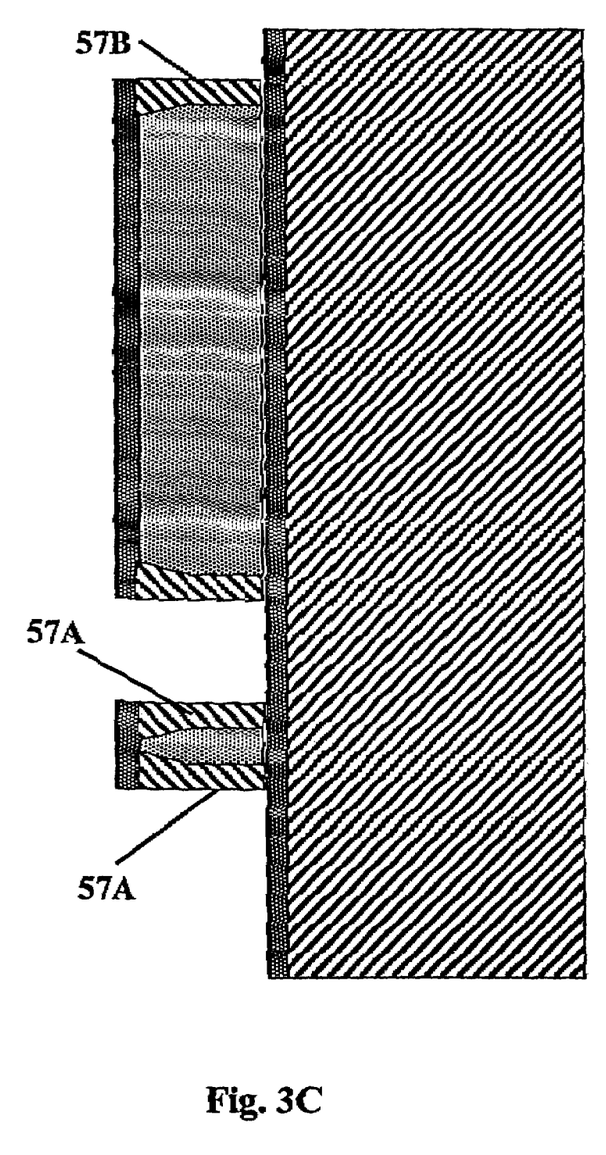
Figure 3D:
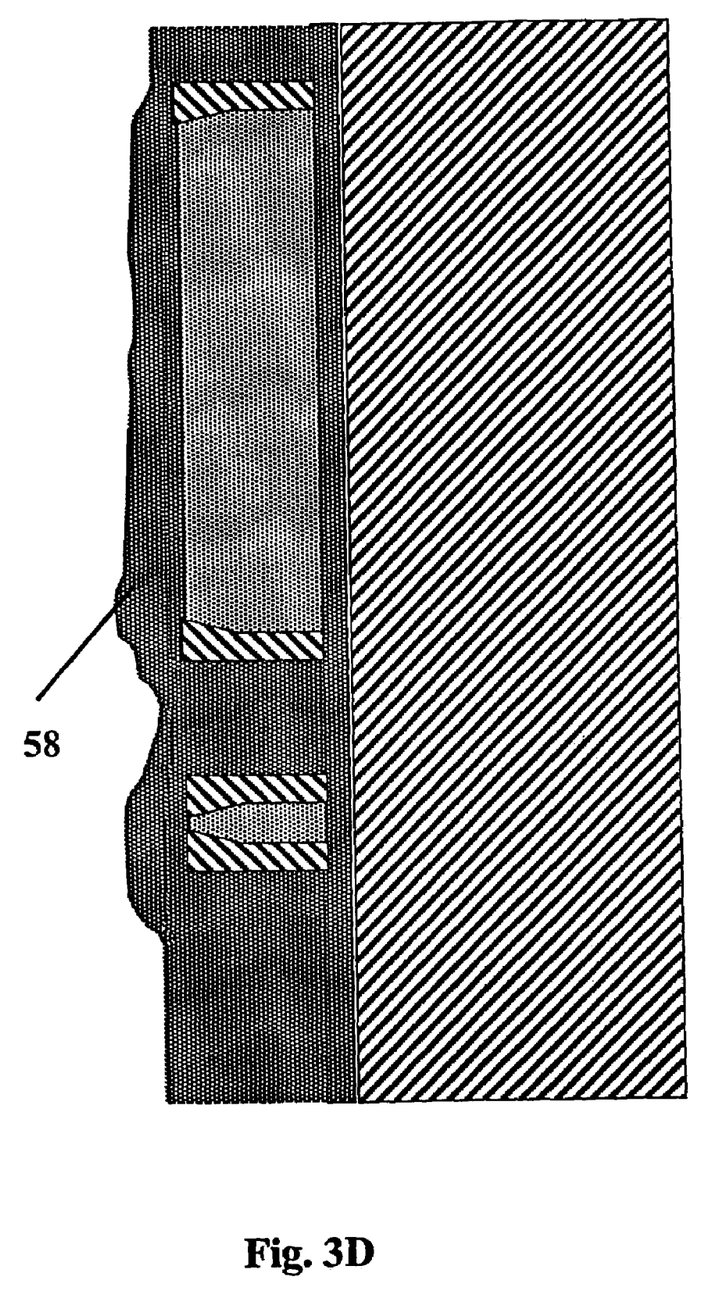
Figure 3E:
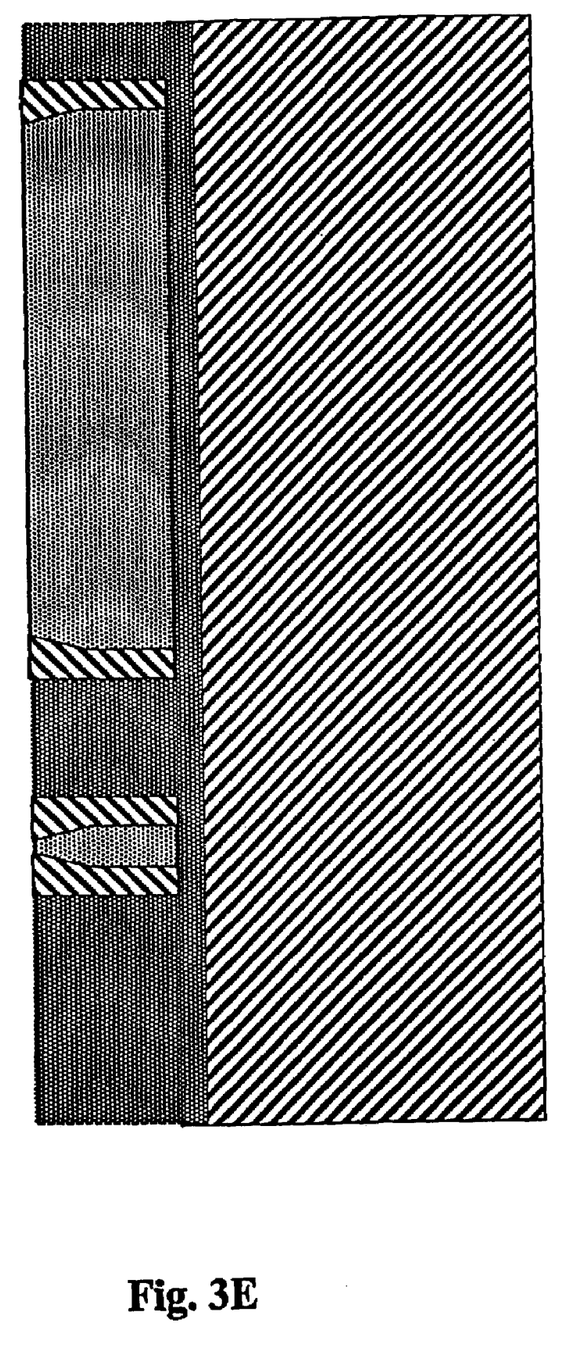

The surface-initiated oxidative conversion reaction is conducted to convert most of the material in the third layer to a cladding 57A of the resistive form, leaving a core 56 in the original form (shown in FIG. 3C). Ancillary cladding 57B is formed, but is not utilized. Material 58 is deposited to fill in the space between the pillars 55 and structural elements 59, to obtain the structure of FIG. 3D. Portions of this material 58, and optionally portions of the pillars 55 and structural segments 61, such as the segments 54A, are removed to make a planar modified third layer 53C (FIG. 3E), which includes modified material fill 58A, and segment 53D.

Figure 3F:
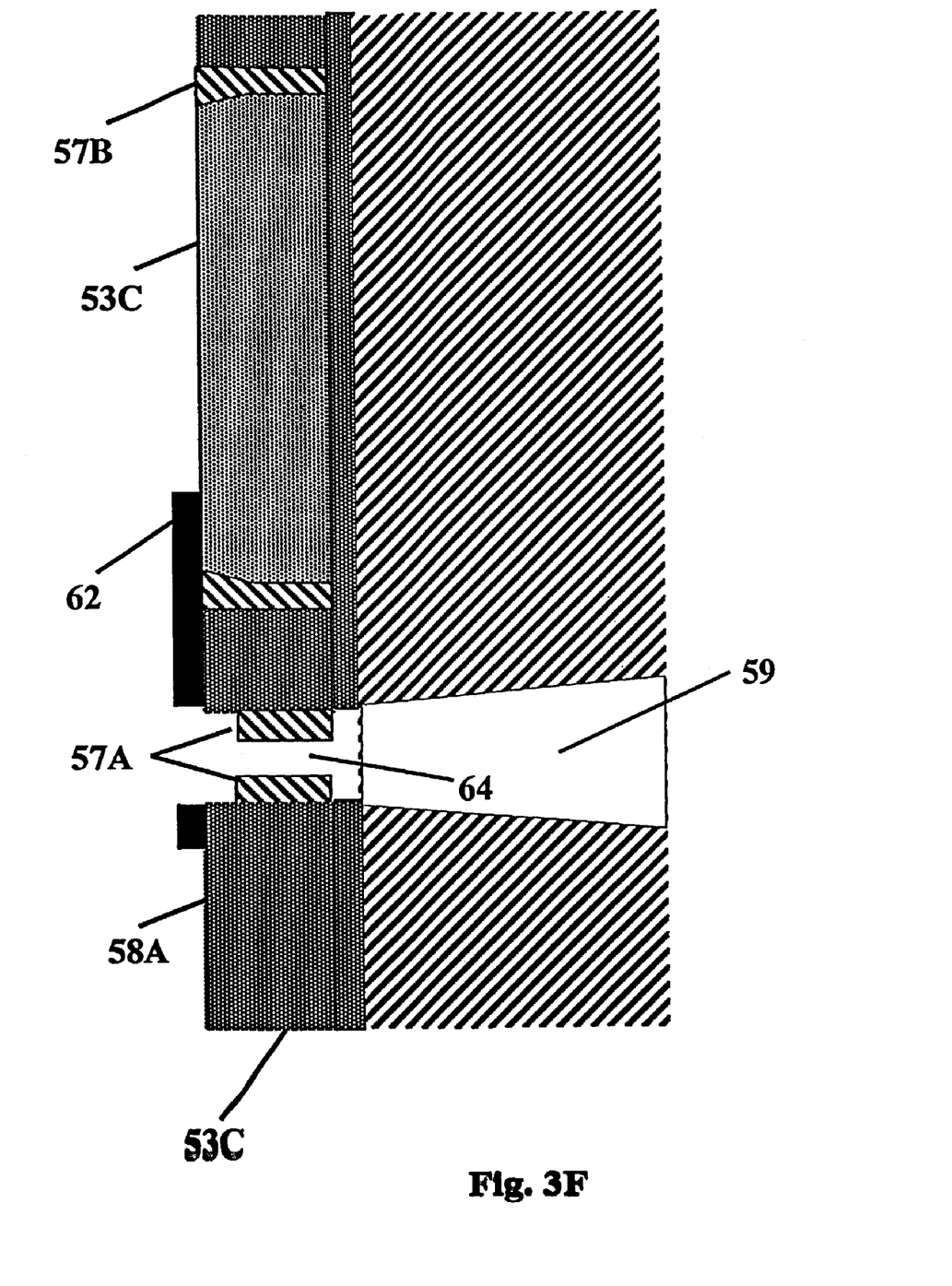

An isotropic etching technique is used to convert the cores 56 to channels 64, which preferably have width of from about 1 nm to about 100 nm, preferably about 5 nm to about 25 nm (FIG. 3F). Thereafter, the first layer 51 can be etched to make interior cavities 59 linked to the channels 64. Electrical leads 62 can be applied by, for example, evaporation techniques.

The channels of the invention can be formed of a single substrate in that, while the forming techniques of the invention can re-form portions of the substrate etched away, no significant, channel-forming substrate must be applied to form a new substrate layer. The channels can also be formed with a single surface-initiated oxidative conversion reaction. Also, the channels can be formed in a single layer of material. Further, the channels do not need to be formed by the intersection of two channels formed in separate substrate layers. Additionally, the channels can be round or oval in cross-section, or have an extended slot shape with the small scale width typical of the invention being the width of the slot (and not the length). Also, at least some of the channels in an array need not be periodically arrayed.

Fourth layers 4 or 54 can be formed, for example, of silicon nitride ($Si_3N_4$) or another material that resists oxidation or otherwise being converted by the surface-initiated oxidative conversion reaction that converts portions of third layers 3 or 53 to a resistive form. Other useful materials include, for example, silicon oxide ($SiO_2$) or silicon carbide (SiC).

Third layers 3 or 53 can be formed, for example, of epitaxial silicon or another material susceptible to a surface-initiated oxidative conversion reaction, which reaction converts the material to a resistive form. Epitaxial silicon is silicon grown by metal organic vapor deposition (MOCVD) or other crystalline growth techniques onto a substrate. This and all materials that will be exposed to the surface-initiated oxidative conversion reaction are selected to physically withstand such treatment, which can include high temperature such as 1,100 degrees Celsius.

Figure 2:
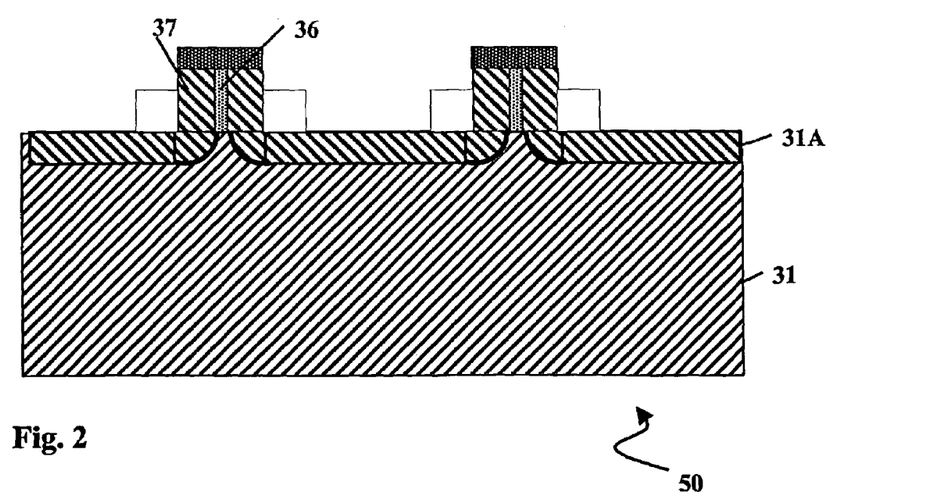
FIG. 2 illustrates another embodiment of the electrical sensor.

Second layers 2 or 52 can be formed, for example, of silicon oxide or another material that (i) resists oxidation or otherwise being converted by the surface-initiated oxidative conversion reaction that converts portions of third layers 3 or 53 to a resistive form or (ii) resists the anisotropic etching process that will be used to create the interior cavities 9 or 59. Other useful materials include, for example, silicon nitride or silicon carbide. As mentioned, this layer is optional. As illustrated in FIG. 2, where this layer is missing, and the analogous first layer 31 is susceptible to the surface-initiated oxidative conversion reaction, nonetheless an unreacted core 36 is formed together with cladding 37 and an oxidized portion 31A of the first layer 31. Even if oxidized portion 31A resists the etching technique used to form interior cavities, it will be apparent that useful interior cavities will be formed.

The fourth layer, or even the use of any distinct layers is further optional. For example, where there is no fourth layer, the smoothing process typically used after filling in between the pillars can be operated to remove segments where the surface-initiated oxidative conversion reaction has created resistive forms that would otherwise block the channels. Or, as illustrated in FIG. 2, the effect of surface-initiated oxidative conversion reactions lower in the substrate can be accommodated without significant penalty.

First layers 1 or 51 can be formed of any material that can be shaped to form interior cavities and provides mechanical support for the other layers. This layer can be formed, for example, of silicon, quartz, alumina, gallium arsenide or germanium.

The channels can be surface modified as needed to render the channels compatible with any molecular species to be incorporated in the channels.

It should be apparent that the first layers 1 or 51 can be bonded or fused to other substrates, to provide support, additional plumbing connections to the interior cavities, portions of the interior cavities, or the like. One manner in which such joining can be effected is by using a heat fusible agent such as a glass glaze, which can for example be applied to the substrate to be added. Or, the materials can be joined by field assisted thermal bonding. Other bonding techniques include anodic bonding, polymerization-assisted chemical bonding, adhesive bonding, or the like. The use of gaskets provides one useful sealing technique.

An example of a surface-initiated oxidative conversion reaction is thermal oxidation of silicon, for example as described in Kao et al., "Two-Dimensional Thermal Oxidation of Silicon—II: Modeling Stress Effects in Wet Oxides," IEEE Trans. Elec. Dev. EO-35: 25–36, 1988.

Figure 3G:
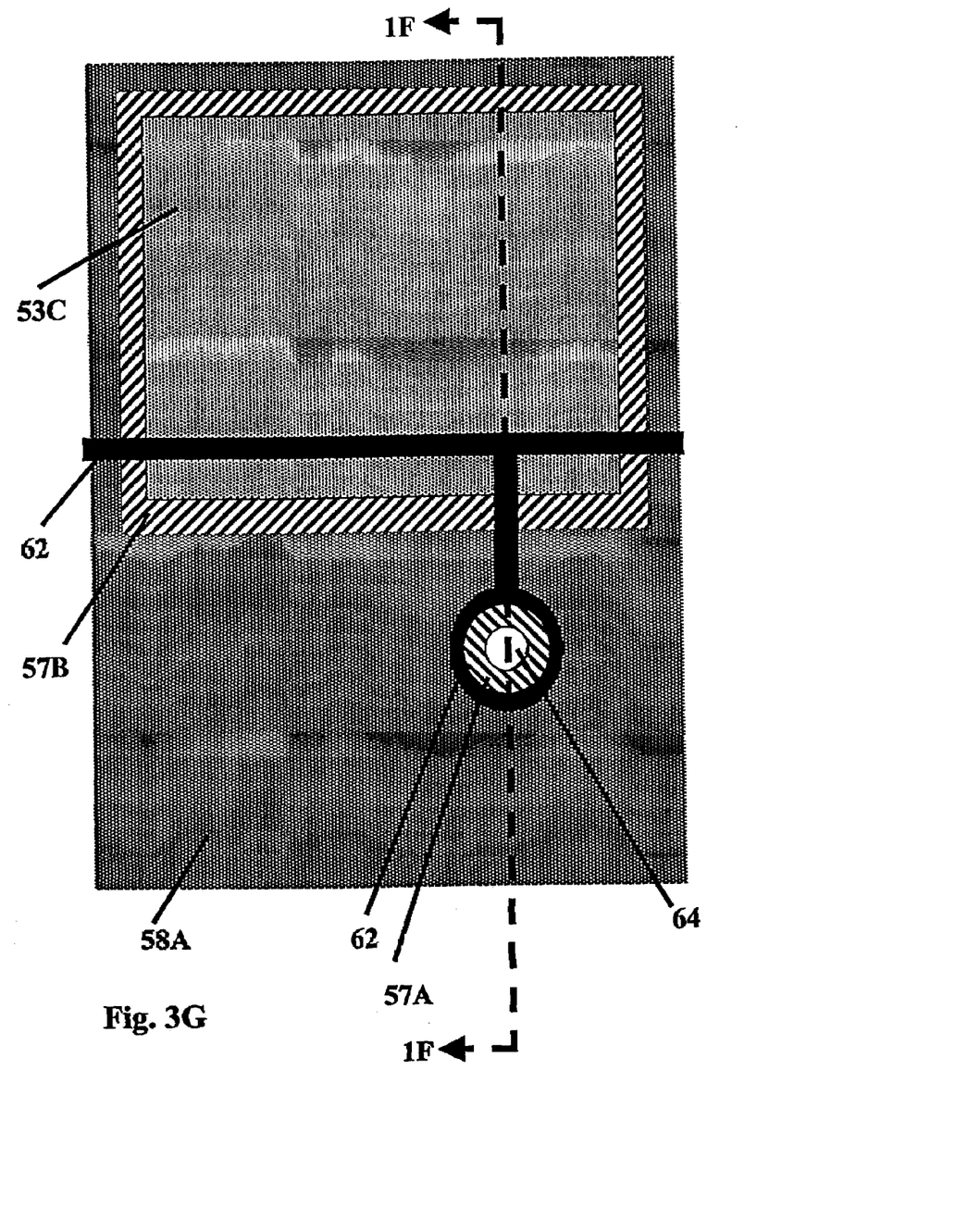

Operation of the device requires monitoring of a current through all or portions of the channels 8. Thus, electrical leads are preferably incorporated into the device, as illustrated in FIG. 3. The conductive pattern is, for example, formed from gold that has been applied to the by standard photolithographic techniques. Counter electrodes can be relatively large, acting as the counter or ground electrode for a number of primary electrodes, or individual. Such electrodes can be incorporated into the sandwiched substrate described here or separate.

The electrical meters used in the invention can include any known in the art. Such meters include low noise, small signal current amplifiers used in the patch clamp art, such as the Axopatch 200A or Dagan 3900A devices.

The channels of the electrical sensors can be modified to attach molecules that affect an electrical property that can be detected through the channels. For example, such molecules can be molecules containing ion exchange moieties, enzymes that affect the electrical properties of the fluid in the channels in a manner that depends on the composition of such fluid, molecules containing moieties that bind or retard the flow of macromolecules in the channels with consequent effects on electrical properties through the channels, and the like. Such fluid can include gases.

Electronics can be attached or incorporated to selectively monitor channels, as is known in the art. Where voltage-sensitive biological molecules are used, voltage addition circuits can be used to selectively activate channels. For example, where voltage-gated ion channels are incorporated into biological membrane across the channel, a matrix addressing system can be used to provide the voltage-activating voltage at the channel under active monitoring. Thereafter, the activating voltage is moved to another channel. Such an operating protocol allows the use of fewer monitoring devices, as all or subsets of the channels are monitored serially.

Electrical sensors of the invention can be used in probes, for example the size of a chalk, for liquid or gas detection. For gaseous detection, a gas-liquid interface can be used, such as a semi-permeable membrane enclosing a saline reservoir exposed to the array. A gas species of interest permeates through the membrane, dissolves in solution and is detected by the sensor array. Each electrical sensor in an array can independently measure the real time binding effect of analytes on fixed receptors. Pattern analysis of responses from all distinct sensors can provide a "fingerprint" of an unspecified analyte, allowing the identification as well as the measurement of its binding properties to all the receptors in the array.

One area of use for the electrical sensors is in high throughput drug screening. Currently, a potential drug candidate is tested against a traditional, highly specific assay of the expected drug target. Such high specificity methods do not effectively measure weak interactions with the drug target. With weak interaction data, one can further explore the components of drug affinity, to provide more detailed drug modeling data. Also, weak interactions to a non-target molecule can be indicative of unintended side effects. Arrays of the invention can monitor weak interactions with hundreds of biomolecules simultaneously.

Arrays of the invention utilizing low selectivity biomolecules can provide an electronic "tongue", where the recognition of complex binding pattern from few receptors. Such an array can be used in viniculture to provide after signatures for desirable blends. Such an array can use transmembrane receptors of the human tongues, functionalized in the sensor array.

Publications and references, including but not limited to patents and patent applications, cited in this specification are herein incorporated by reference in their entirety in the entire portion cited as if each individual publication or reference were specifically and individually indicated to be incorporated by reference herein as being fully set forth. Any patent application to which this application claims priority is also incorporated by reference herein in the manner described above for publications and references.

While this invention has been described with an emphasis upon preferred embodiments, it will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention as defined by the claims that follow.

What is claimed:

1. A method of forming a solid phase array of electrical sensors comprising: forming pillars on a surface of a substrate; conducting a surface-initiated oxidative conversion reaction to convert the lateral exterior of the pillars to a form more resistive to an isotropic etching process, while not converting cores of the pillars; conducting an etching process to form channels from the cores; forming larger cavities in the substrate beneath and connected to the channels, and forming electrical leads on the substrate connected to both sides of each of the channels, such that, when attached to an appropriate metering device, voltages, currents or resistivities through the channels can be measured.

2. The method of claim 1, further comprising: filling the space between the pillars with a material; and forming a smooth surface of the substrate adjacent to where the channels exit the substrate.

3. The method of claim 1, wherein the formed channels have a diameter of about 25 nm or less.

4. The method of claim 1, wherein the formed channels are round or oval in cross-section.

5. The method of claim 1, wherein the formed channels have an extended slot shape.

6. The method of claim 1, further comprising incorporating one or more biological polymeric molecules into the formed channels.

7. The method of claim 2, wherein the formed channels have a diameter of about 25 nm or less.

8. The method of claim 2, wherein the formed channels are round or oval in cross-section.

9. The method of claim 2, wherein the formed channels have an extended slot shape.

10. The method of claim 2, further comprising incorporating one or more biological polymeric molecules into the formed channels.

* * * * *